(12) United States Patent
Moore (10) Patent No.: US 6,387,049 B1
(45) Date of Patent: May 14, 2002

(54) COMPUTER-ASSISTED METHOD FOR ANALYZING CONSUMPTIONS

(76) Inventor: Steven Jerome Moore, 58 Butterfield Rd., Newtown, CT (US) 06470

( * ) Notice: Subject to any disclaimer, the term of this patent is extended or adjusted under 35 U.S.C. 154(b) by 0 days.

(21) Appl. No.: 09/491,844

(22) Filed: Jan. 26, 2000

Related U.S. Application Data

(63) Continuation of application No. 09/185,133, filed on Nov. 3, 1998, now Pat. No. 6,032,676, which is a continuation of application No. 08/581,889, filed on Jan. 2, 1996, now Pat. No. 5,836,312.

(51) Int. Cl.⁷ .............................................. A61B 19/00
(52) U.S. Cl. ...................................................... 600/300
(58) Field of Search ........................... 128/921; 600/300

(56) References Cited

U.S. PATENT DOCUMENTS

| | | | |
|---|---|---|---|
| 4,321,674 A | 3/1982 | Krames et al. ........ | 364/413.29 |
| 4,686,624 A | 8/1987 | Blum et al. ............ | 364/413.29 |
| 4,855,945 A | 8/1989 | Sakai ..................... | 364/413.29 |
| 4,894,793 A | 1/1990 | Ikemoto et al. ........ | 364/413.29 |
| 4,924,389 A | 5/1990 | Gerbaulet et al. ..... | 364/413.29 |
| 4,954,954 A | 9/1990 | Madsen et al. ........ | 364/413.29 |
| 5,233,520 A | 8/1993 | Kretsch et al. ......... | 128/921 |
| 5,412,560 A | 5/1995 | Denniston .............. | 128/921 |
| 5,412,564 A * | 5/1995 | Ecer ....................... | 128/921 |
| 5,836,512 A | 11/1998 | Moore .................... | 128/921 |
| 5,897,493 A * | 4/1999 | Brown .................... | 600/300 |

* cited by examiner

Primary Examiner—William E. Kamm (57) ABSTRACT

A computer-assisted system and method for adjudging the effect of consumable intakes on physiological parameters is disclosed wherein a consumer records in a database a plurality of consumable identifiers identifiying consumables consumed, the amounts of each consumable consumed, times of consumption of each consumable, a plurality of physiological measurements and time of physiological measurements, and such information is computationally related to consumption information, such as nutritional information, linked to the consumable identifier in another database.

7 Claims, 8 Drawing Sheets

COMPUTER-ASSISTED METHOD FOR ANALYZING CONSUMPTIONS

RELATED APPLICATIONS

This is a continuation filed under filed under 37 C.F.R. §1.52(b) of U.S. Pat. application Ser. No. 09/185,133, filed Nov. 3, 1998, now U.S. Pat. No. 6,032,676, which is continuation of U.S. patent application Ser. No. 08/581,889, filed Jan. 2, 1996, now U.S. Pat. No. 5,836,312, from which priority is claimed, and which are incorporated by reference in their entirety herein.

BACKGROUND OF INVENTION

1. Field of Invention

The present invention relates generally to an apparatus and method for correlating daily consumable intakes with physiological parameters. More specifically, it relates to a computer-assisted system and method for adjudging the effect of consumable intakes, such as the amount of calories, fat, protein, carbohydrate, minerals and vitamins consumed daily, or the amount of a drug ingested daily, on physiological parameters, such as weight, blood glucose levels, or red blood cell count.

2. Brief Description of the Prior Art

A great body of literature has been published in the last fifty years pertaining to the importance of good consumption habits in the maintenance of health. While the general public is far more educated as to such matters than their ancestors, several studies suggest poor consumption habits still pervade in our society.

Nutritional studies suggest that people today continue to consume foods containing high amounts of saturated fat, too many calories, and too few vitamins and minerals, although they know these foods to be "unhealthy." Likewise, public awareness of the fact that drugs may cause serious side-effects, has not eventuated in a substantial reduction in the misuse and over-use of, for example, over-the-counter medications. A significant factor in many people's poor diets and abuse of medications is the tremendous explosion of multi-ingredient pre-packaged foodstuffs and drugs. that has occurred within the last century.

In response to an outcry of world-wide health experts with respect to less than "healthy" ingredients not infrequently found in pre-packaged consumables, many governments have mandated that manufacturers of pre-packaged consumables provide in their labelling certain consumption information such as the identity of the ingredients, the concentration of ingredients and/or nutritional information. In the United States foodstuff information not atypically includes the ingredients contained within the foodstuff, the number of calories in a serving, the number of servings in a container, the percentage of fat, protein, carbohydrates provided by a serving, and a measure of the vitamins and minerals provided by the foodstuff. Over-the-counter medications are not infrequently labelled to delineate the drug products, and concentration of drug products, contained within each tablet of the medication.

In order to keep the public more informed concerning the foodstuffs they eat, some governments have further required manufacturers to compare the nutritional contents of their products against a standard daily nutritional recommendation, e.g. the "Daily Value" or "Recommend Daily Allowance" or "Minimum Daily Allowance." Such comparisons are often made in terms of percentages. While such information has gone a long way towards educating people with respect to the nutritional value of what they eat, most people do not have the time or patience to consider whether the foods they eat over a day, week or month are providing them with a nutritionally balanced diet. The latter observation is confirmed by the large number of obese people in the Western World.

In a similar vein, many governments require manufacturers of drugs to label their drugs with warnings concerning the side-effects that maybe elicited by consumption of the drug. While most consumers are aware of the existence of warning labelling, few people take the time to read all of the warnings appended with every drug which they consume daily. This is particularly true with respect to over-the-counter medications. Side-effects caused by these drugs are often attributed to other causes.

Presently, monitoring of dietary and medication consumption, as well as the consumption of other consumables, is cumbersome. Such monitoring is conventionally done by use of log books in which the subject records the consumables, and the quantity of consumables consumed during a particular day.

Nutrition counseling not uncommonly involves the use of complex algorithms and calculations. Dietary diligence or the use of restricted menu lists is frequently prescribed in a universal manner, rather than tailoring the counseling to the individuals themselves. Nearly everyone is familiar with diet books which propound strict regimens of meals or which limit food consumption to particular food stuffs. More recently, cards which permit persons to select form a prolifery of food stuffs in select categories have been introduced. While easier to follow than strict dietary regimens, such cards fail to take into account the widespread "cheating" that occurs by persons throughout the day. Specialized meals are not always available to a person during the day, especially at work.

Counseling with respect to drug use is presently limited mostly to consultations with pharmacists and physicians. Consultations with physicians tend to be brief and nearly always center on the appropriate use of prescribed medications. Consultations with pharmacists while generally longer, and while often concerning both prescription and over-the-counter medications, are often limited by the ever-increasing time constraints being placed on pharmacists to fill more prescriptions per hour. As with nutritional consultations, drug consultations frequently involve the use of algorithms, especially in regard to the determination of when steady-state blood levels, or maximum blood levels, of a drug given on a repeated dosage schedule will be achieved. Variations in physiological parameters often plateau when drug blood concentrations level off.

The monitoring of consumable intake, especially with regard to nutritional balance and drug intake, is arguably as important as the monitoring of such physiological parameters as blood pressure and pulse rate alone. Numerous computerized devices have been introduced to record and display physiological parameters, see e.g. U.S. Pat. No. 4,232,682 (temperature, pulse rate, and respiration rate). Such devices have greatly aided physicians in tailoring therapeutic strategies to the individual especially if such measurements are taken over a long period of time. For example, a patient's drug therapy is often based on multi-daily blood pressure readings taken by a patient with a computerized blood pressure monitor, such multiple readings being far more indicative of the patient's blood pressure status than one isolated.reading at the physician's office.

Nutritional status has long been known to impact greatly upon physiological homeostasis. Over the past two centuries, scientists have discovered numerous components in our foodstuffs that are necessary to our health—many of these substances being referred to as "essential vitamins." In the last half of the twentieth century, scientists further discovered that many substances present in foodstuffs, while not needed by the body for immediate survival, greatly aid in the maintenance of good health—e.g. fiber and "non-essential vitamins". Scientists further learned that balance in protein/fat/carbohydrate consumption is also of importance in longevity.

In a similar vein, consumption of drugs, while often ameliorating a perturbation in homeostasis, not infrequently cause physiological abnormalities themselves. This effect is often noted when patients chose over-the-counter ("OTC") drugs without the aid of health professionals. For example, decongestants may increase blood pressure.

Consumable intakes may have significant effects upon the morbidity rate of persons inflicted with several diseases. Many people require a special diet which places their nutritional needs outside of the standard daily nutritional recommendation. Further, many people can not consume certain drugs which are freely available in OTC preparations.

For example, diabetics are often cautioned by their physicians to carefully monitor their daily intake of protein, fat and carbohydrates. For many diabetics, variations in dietary consumption, especially of carbohydrates, can have dramatic effects on their requirement for insulin. Different foodstuffs not uncommonly have different effects on a person's blood glucose level, a level which is important for good heath. Blood glucose measurements are taken by diabetics numerous times during the day, especially after meals. Diabetics are frequently warned to refrain from cough preparations etc., which contain high sucrose concentrations.

Consonantly, persons afflicted with Folling's disease ("PKU") must be careful with respect to their consumption of foods containing phenylalanine. Person's with Folling's disease have a congenital abnormality which eventuates in a deficit of phenylalanine 4-monoxygenase activity. Consumption of phenylalanine by PKU patients over prolonged periods of time may result in neurologic abnormalities. Person's with Folling's disease not uncommonly monitor their blood or urine phenylalanine levels daily.

As further example, persons with depression are not infrequently placed on monoamine oxidase inhibitors. Persons on the drug (and 2 weeks after discontinuing the drug) are cautioned against eating foods with high tyramine or tryptophan content. They are further cautioned about consuming drugs which contain decongestants. Consumption of any of these consumables may lead to a hypertensive crisis.

While much is known pertaining to the physiological effect of certain consumables in select maladies, little has been done to relate the effect of daily consumption of the multitude of consumables to physiological perturbations. The latter is most likely due to the difficulty in getting subjects to record their daily consumptions and the need to solve often complex algorithms in order to appropriately adjudge such relationships.

A relatively recent development in the consumable processing art, as well as product sales in general, has been the identification of a consumable by a unique identifier encoded in the form of a "bar code". Heretofore, the bar code has been used to identify the product and its manufacturer, used to re-order goods and employed at check-out counters for coupling the product to a price.

OBJECTS AND SUMMARY OF PRESENT INVENTION

It is an object of the present invention to provide a computer-assisted system and method for electronically coupling consumption information with respect to consumables, including, but not limited to, food stuffs, drugs, cosmetics, with consumable-identifiers, for retrieving such consumption information upon input of a consumable-identifier, and for computationally-relating the consumption information from one consumable with the consumption information from a plurality of other consumables.

It is a further object of the present invention to provide a method and apparatus which permits correlation of human physiological parameters, such as body weight or blood glucose levels, with consumable intake over set time periods.

In one embodiment, a foodstuff identifier is linked in a first database to the nutritional information generally provided on pre-packaged foodstuffs, or is linked to estimated nutritional information with respect to a non-prepackaged foodstuffs. Using an electronic means, a consumer of the foodstuff converts the foodstuff identifier on the packages of the pre-packaged foodstuffs, or the foodstuff identifiers associated with the non-prepackaged product in a book, manual, database or other compendium, which are consumed during the day into a digital datastream which is downloaded into a second data processing unit which is processed along with time data with respect to the time of consumption and stored in a second database. Along with the foodstuff identifiers, the consumer may also input approximate serving size or amount consumed, thereby storing digitalized information in the second database regarding the foodstuff consumed, the amount of each particular foodstuff consumed, and the time of consumption. Physiological measurements such as weight gain, or blood sugar concentrations may also be input into the second database coupled with time data. At set time intervals, typically daily or weekly, the consumer sends to a first data processing unit connected to the first database the digitalized information stored in the second database. The first data processing unit correlates the nutritional information pertaining to each foodstuff reported to have been consumed during the time interval and with computational manipulation, adjusting for amount consumed, provides a readout of nutritional parameters, such as total calories or carbohydrates, consumed over the time period. Recommendations for improving the diet may be addended to the readout of the nutritional parameters by linking the recommendations to the results of pre-programmed nutritional algorithms or manually by a nutritionist or other qualified professional. If physiological measurements were also input, the first data processing unit may use algorithms well-known in the art to determine whether variations in physiological measurements may be related to foodstuff consumption.

In another embodiment, a consumable (such as a drug) identifier is linked in a first database connected to a first data processing unit to the ingredient information generally provided on pre-packaged consumables, or is linked to estimated ingredient information with respect to a non-prepackaged consumables. Using an electronic means, a consumer of the consumables converts the consumable identifier on the packages of the pre-packaged consumables, or the consumable identifiers associated with the non-prepackaged consumable in a book, manual, database or other compendium, which are consumed during the day into a digital datastream which is downloaded into a second data processing unit which is processed along with time data with respect to the time of consumption and stored in a second database. Along with the consumable identifiers, the consumer may also input the amount consumed, thereby storing digitalized information in the second database regarding each consumable consumed, the amount of each consumable consumed, and the time of consumption in the second database. Physiological measurements such as blood pressure or pulse rate may also be input into the second database coupled with time data. At set time intervals, typically daily or weekly, the consumer sends to a first data processing unit connected to the first database the digitalized information stored in the second database. The first data processing unit correlates the ingredient information stored in the first database with each consumable reported to have been consumed during the time interval. The data processing unit in such embodiment is programmed such that it recognizes changes in the measured physiological parameter having been measured over the defined time period and such that it can relate known effects and side-effects of the consumed ingredients with the measured parameter. For example, it is well-known in the art that sympathomimetic drugs can increase blood pressure. An increase in blood pressure over time can be computationally related to an increase in sympathomimetic consumption. Further, it is well-known in the art that most drugs following first order kinetics will reach steady-state blood concentrations after approximately four half-times. The processing unit can be provided with such half-time information such-that it can be determined if any change of the measured physiological parameter dissipates after the four half-times of each ingredient transpires—such dissipation strengthening the conclusion that the drug is leading to an change in the measured parameter. Recommendations for adjusting the consumption habits of the consumer may be generated by means of a program or manually by a pharmacist, pharmacologist, toxicologist, physician, nurse or other qualified professional.

The present invention covers the concept that the first database and second database may be the same or different databases maintained or housed in the same data processing unit. The present invention also covers the concept that the consumption habits of either humans or animals may be monitored.

There are many possible modifications and changes which could be made to the system without straying from the applicant's present invention. Such modifications would be obvious to those skilled in the art and should not limit the scope of applicant's claimed invention.

BRIEF DESCRIPTION OF THE DRAWINGS

For a more complete understanding of the objects of the present invention, the Detailed Description of the Illustrative Embodiments thereof is to be taken in connection with the following drawing, in which.

DETAILED DESCRIPTION OF THE ILLUSTRATIVE EMBODIMENT OF THE PRESENT INVENTION

Figure 1:
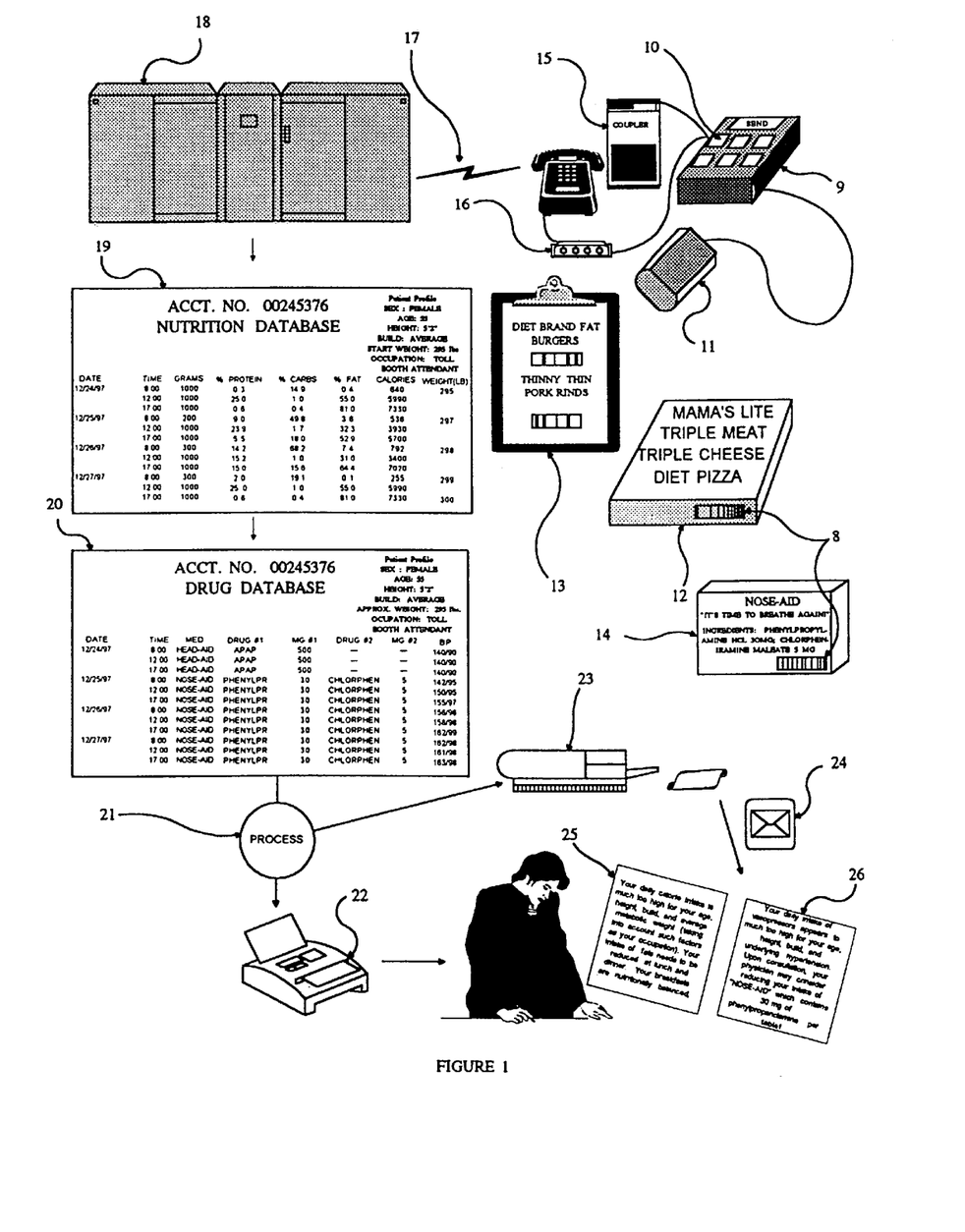
FIG. 1 is schematic flow diagram of a process according to the invention.
Figure 1A:
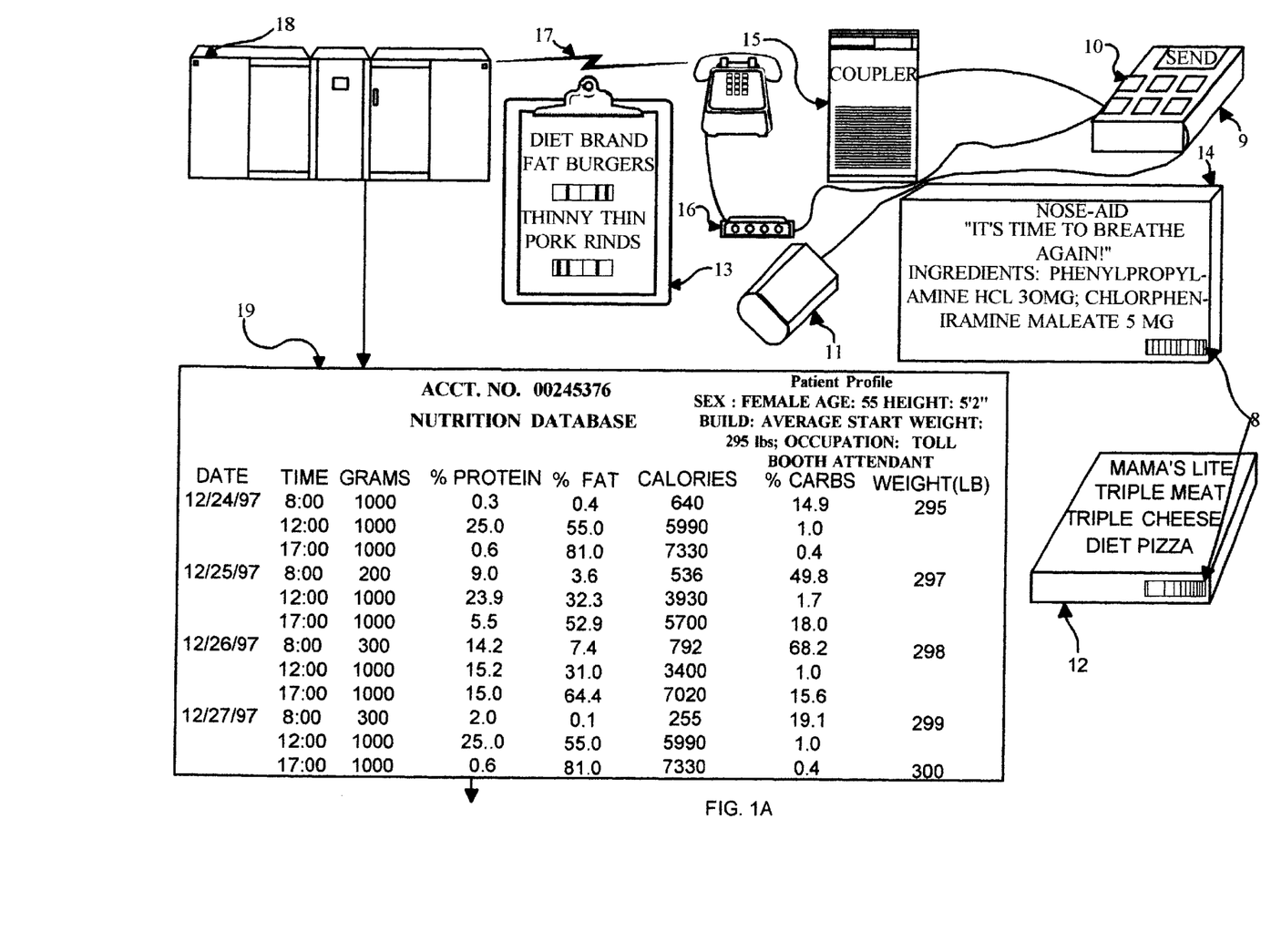
Figure 1B:
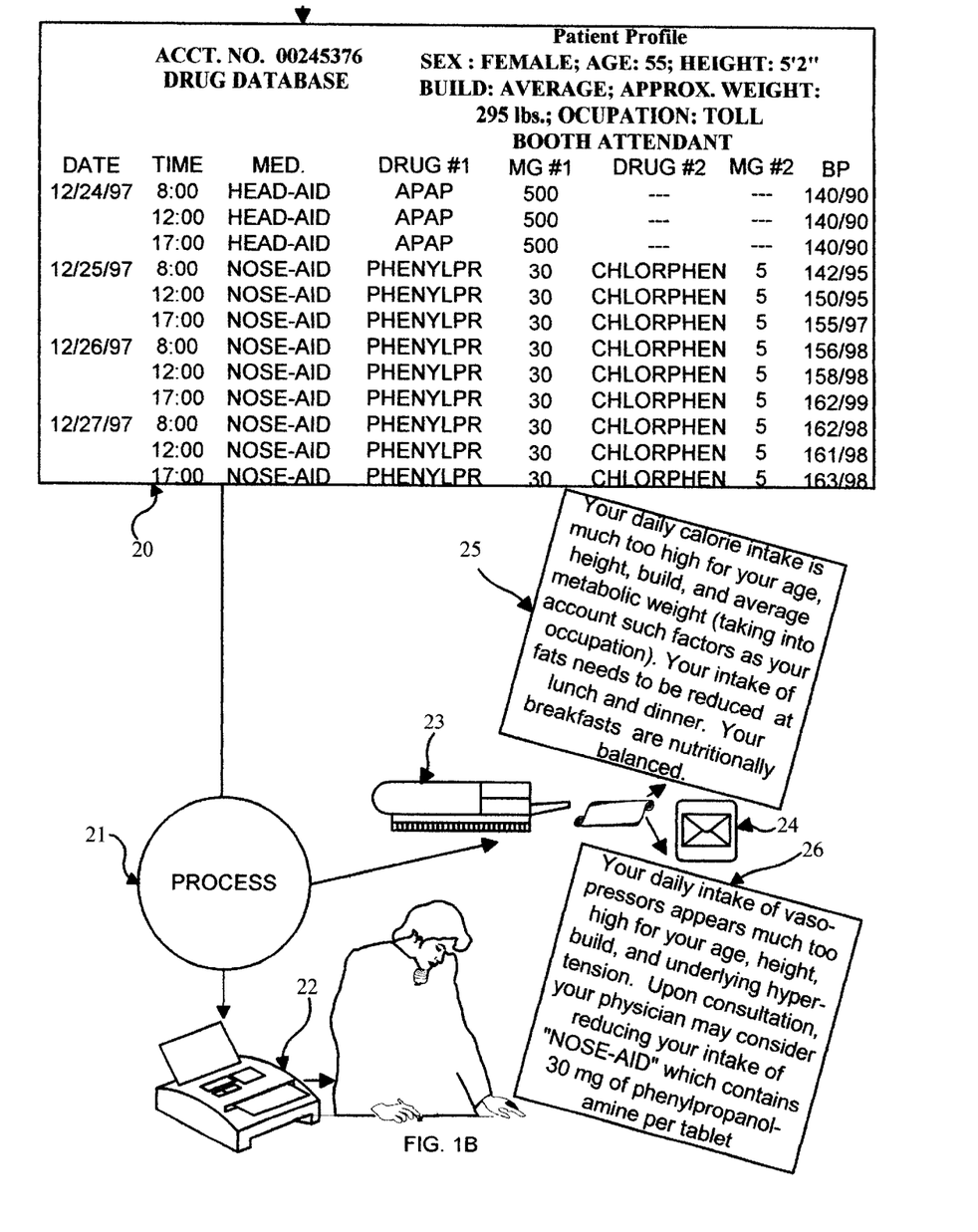

Referring to FIG. 1 of the drawings, there is shown a schematic flow diagram of a preferred embodiment for correlating measurements of human physiological parameters with consumable intakes. Consumable identifier 8 is attached to a consumable, such as a foodstuff 12 or drug 14, or is related in a book, manual, pamphlet or similar compendia to a particular consumable or type of consumable 13. A plurality of first databases, such as nutrition database 19 and drug database 20, is maintained by means of a first data processing unit 18 wherein consumption information of a particular consumable, e.g. nutritional information or ingredient composition information, is related with the consumable identifier. The first databases 18 also contain consumer identification information related to a consumer who is authorized to use the system. Such consumer identification information generally relates to the consumer's name, address and account number as well as certain physiological parameters such as age, height, weight and build. A consumer purchases consumables with identifiers pre-attached, 12, 14, or purchases a book, manual, pamphlet or similar compendia which relates particular consumables, or types of consumables, with consumable identifiers, 13. Each time a consumable is consumed or shortly thereafter, the consumer inputs the consumable identifier, along with the amount of consumable consumed, and the time of consumption into a second database by means of a second data processing unit 9 which may be coupled to an electronic reading device, such as an optical scanner 11 and/or keyboard 10. The second data processing unit 9 if provided with an internal clock may also use the time of entry of the data into the second database as the time of consumption. The consumer may also input physiological data by keyboard 10, or other electronic means, into the second databases, such physiological data including weight and blood glucose concentration, coupled with the time of measurement of the physiological measurement. After a plurality of consumptions and/or physiological measurements, the consumer transmits 17, by means including telecommunication means, as for example modem 16 or phone coupler 15, the data stored in the second database in second data processing unit 9 to the first data processing unit 18 which is electronically coupled to the first databases. The first data processing unit 18 is pre-programmed to computationally relate, after correlating the consumer identification information maintained therein with the consumer identification information maintained in the second database of the second data processing unit 9, the consumable information with respect to a particular consumable stored in the plurality of first databases with the information pertaining to the quantity of that consumable consumed and its time of consumption, maintained in the second database by correlating the food identifiers. The first data processing unit is further pre-programmed with consumption algorithms, such as those well-known in the nutrition and pharmaceutical art, relating consumption parameters to one or more physiological parameters. After processing and computationally relating these parameters 21, second data processing unit 18 is programmed to generate an advisory report advising changes in consumption habits of the consumer, such as changes in foodstuff consumption 25 or drug consumption 26. The electronic readout may be transmitted via telecommunications means back to the consumer, as by facsimile machine 22, or a hard copy printed by printing means 23 can be sent to the consumer by post 24, if both the first data processing means and second data processing means are not housed at in the same location.

Figure 2:
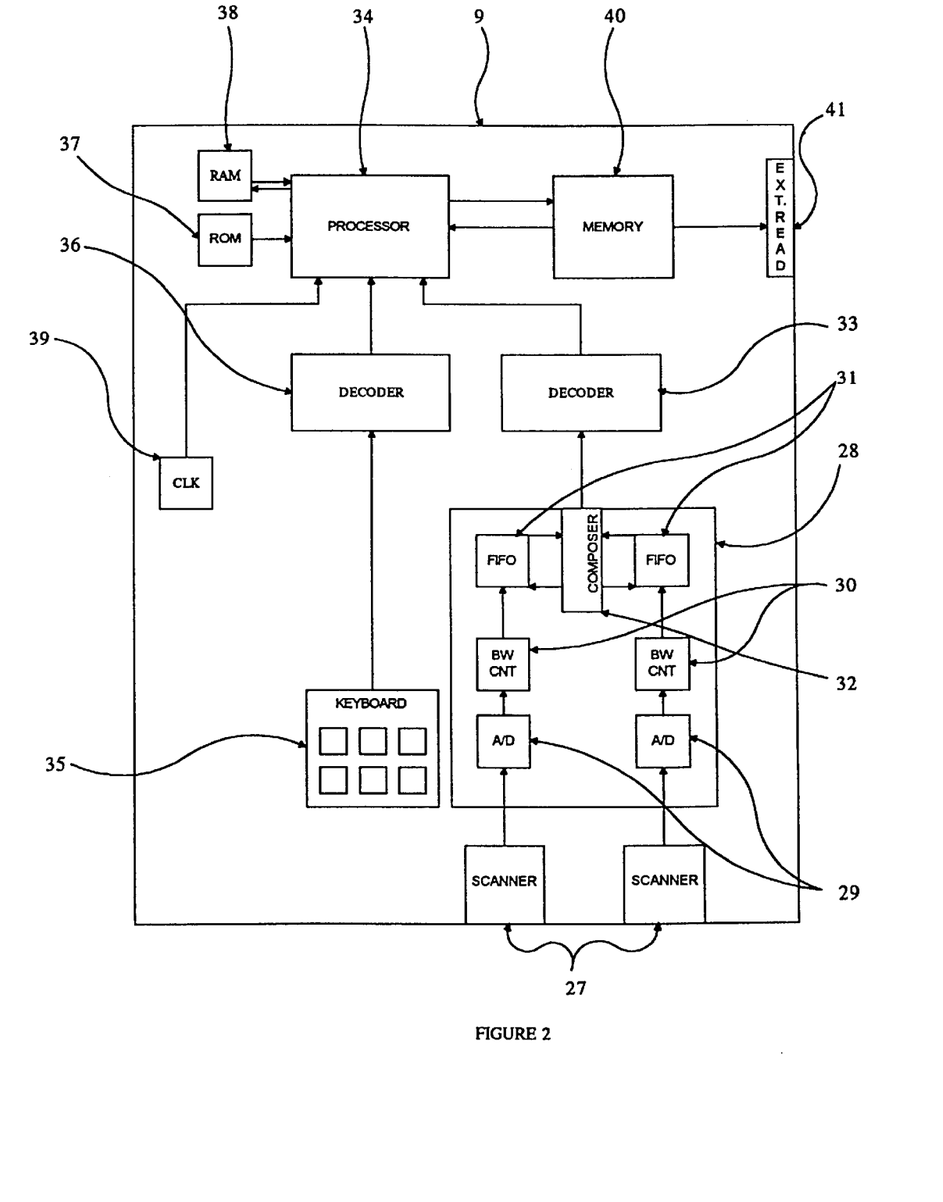
FIG. 2 is a block diagram illustrating a microchip-based device designed to store identifiers pertaining to consumables consumed over time along with time data, and which permits correlation of the same to physiological parameters.

Referring now to FIG. 2, there is shown a block diagram illustrating an embodiment of second data processing device 9 designed to store identifiers pertaining to consumables consumed over time along with time data, and which permits input of physiological parametric data which may be coupled with time data.

In this embodiment of second data processing device 9 optical scanner detectors 27 are housed within the unit rather than connected thereto as shown in 11 of FIG. 1. Optical scanner detectors 27 are coupled to a bar code reader 28 of the prior art, such bar code reader 28 comprising a plurality of analog-to-digital converts 29, bar width counters 30, first-in first-out registers ("FIFOs") 31, and composers 32. Numerical data held in FIFOs 31 are sent to decoder 33 in accordance with a command sent from processor 34. For simplicity, lines for transferring command signals and response signals between processor 34 and other units of bar code reader 28 such as FIFOs 31 and decoder 33 are omitted. Processor 34 is connected to read-only memory ("ROM") 37 used for storing programs used in processor 34 and random-access memory ("RAM") 38 which is used as a work area during processing. Processor 34 processes bar code data sent from decoder 33 and couples the same to time data provided by clock 39. Such processed bar code data is stored in memory storage unit 40. Second data processing device 9 further provides for input of physiological parameter data by keyboard means 35. Such input is decoded by decoder 36 and the physiological data is processed such as to couple it with time data provided by clock 39. Such processed physiological data is stored in memory storage unit 40. Information stored in memory storage unit 40 may be transmitted to first data processing unit 18 through external read port 41 coupled to modem 16, telephone coupler 15, or other communications means.

Figure 3:
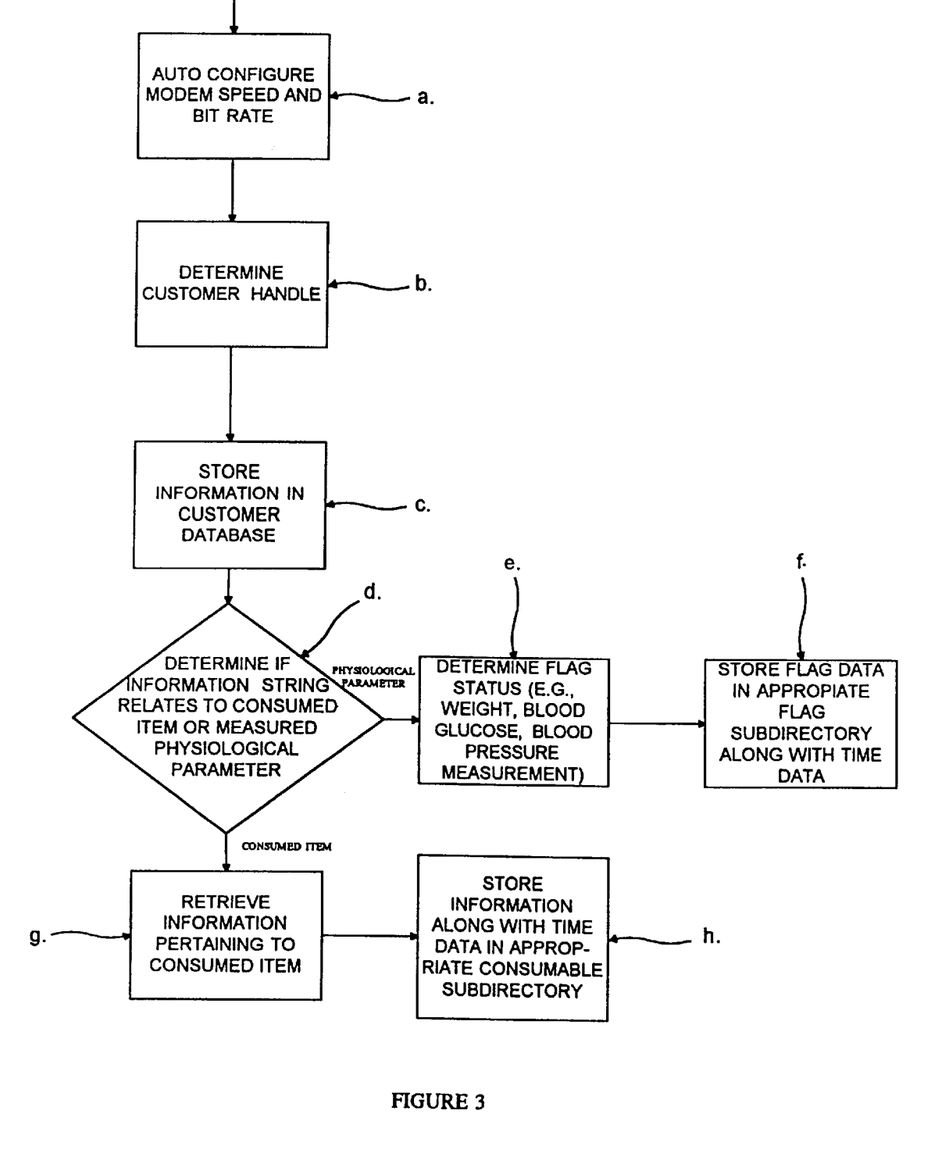
FIG. 3 is a flow chart of a process by which information stored in the microchip-based device of FIG. 2 is downloaded and stored in a first database coupling product identifiers to information concerning the product.

Referring now to FIG. 3, there is shown a flow chart of a process by which information stored in the microchip-based device of FIG. 2 is downloaded and stored in databases of first data processing unit 18 which is programmed to couple product identifiers to information concerning the product. First data processing unit 18 autoconfigures to accept the modem speed and bit rate of incoming data (FIG. 3a) being transmitted from second data processing unit 9. The customer handle is subsequently determined (FIG. 3b) to determine which customer directory the information is to be directed towards (FIG. 3c). Information is stored in customer subdirectories by determining whether the information string relates to a consumed item or measured physiological parameter (FIG. 3d). The type of physiological data, such a weight data, blood glucose data, blood pressure measurement data, etc., is determined (FIG. 3e) and stored along with time data coupled thereto in a subdirectory directed to the physiological measurement (FIG. 3f). In response to consumed item data the first data processing unit may directly store such information along with time data in an appropriate consumable item directory, such as that for food items consumed or drugs consumed, for later processing or it may be programmed to retrieve certain consumable information pertaining to the consumed item (FIG. 3g) and to store the same along with item identification in an appropriate consumable item directory (FIG. 3h).

Figure 4:
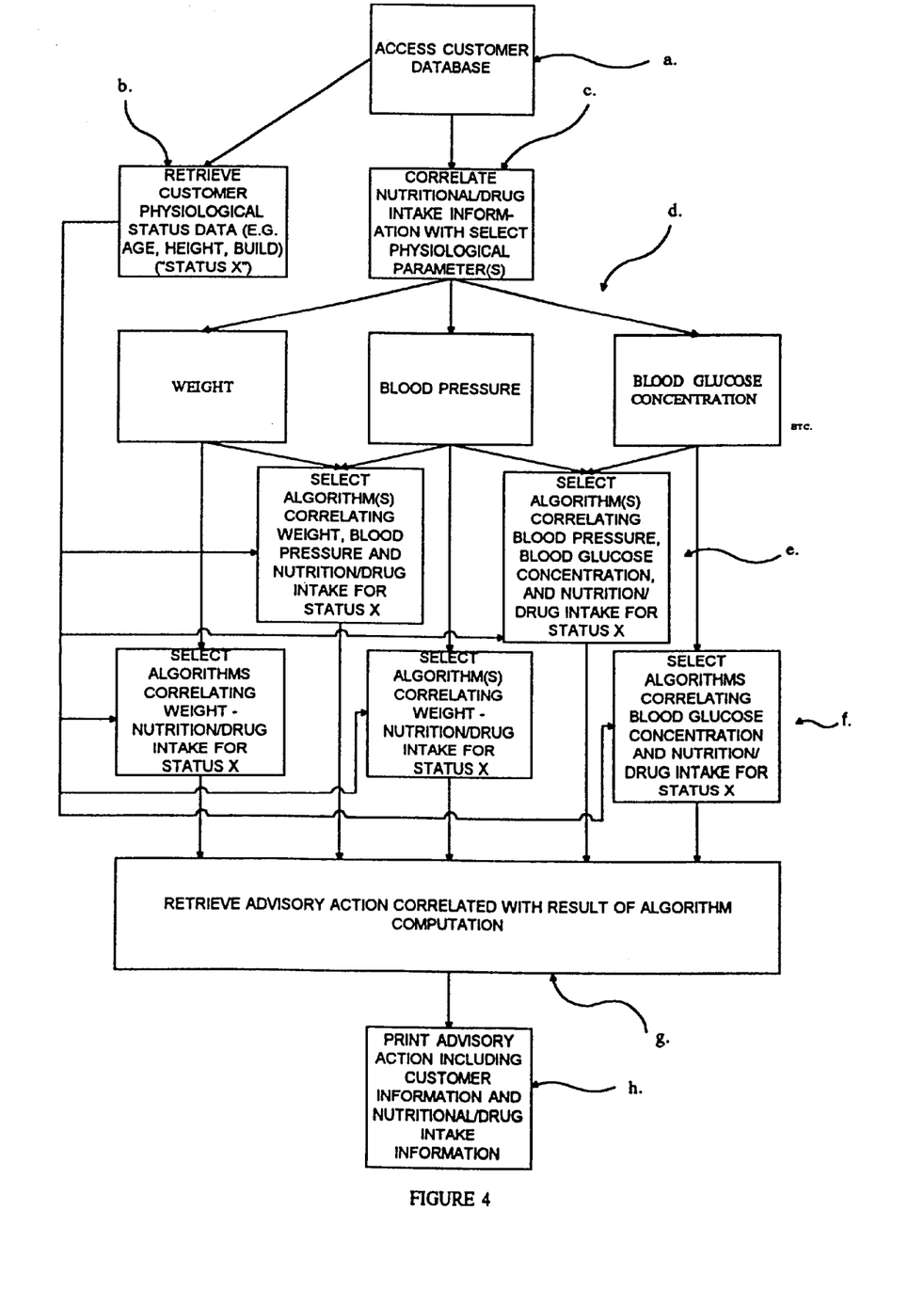
FIG. 4 is a flow chart of a process by which advisory actions pertaining to consumption habits is generated in response to consumable intakes and physiological parameter measurements recorded over time.

Now referring to FIG. 4, there is shown a flow chart of a process by which advisory actions pertaining to consumption habits is generated in response to consumable intakes and physiological parameter measurements recorded over time. Customer database directories and subdirectories are accessed (FIG. 4a), including those directories related to information pertaining to the customer's physiological status, such as age, height, build, etc. (FIG. 4b). Intake information is correlated with the selected physiological parameter(s) of concern (FIG. 4c), as for example foodstuff consumption being correlated with weight and/or blood glucose concentrations, or drug consumption being correlated with blood pressure measurements (FIG. 4d). Algorithms relating the physiological parameter(s) of concern with the type of intake are selected (FIG. 4e,f) and solved. Advisory actions correlated with the result of the algorithm computation are then selected (FIG. 4g) and subsequently printed so as to be directed to the consumer of the consumables (FIG. 4h).

Figure 5:
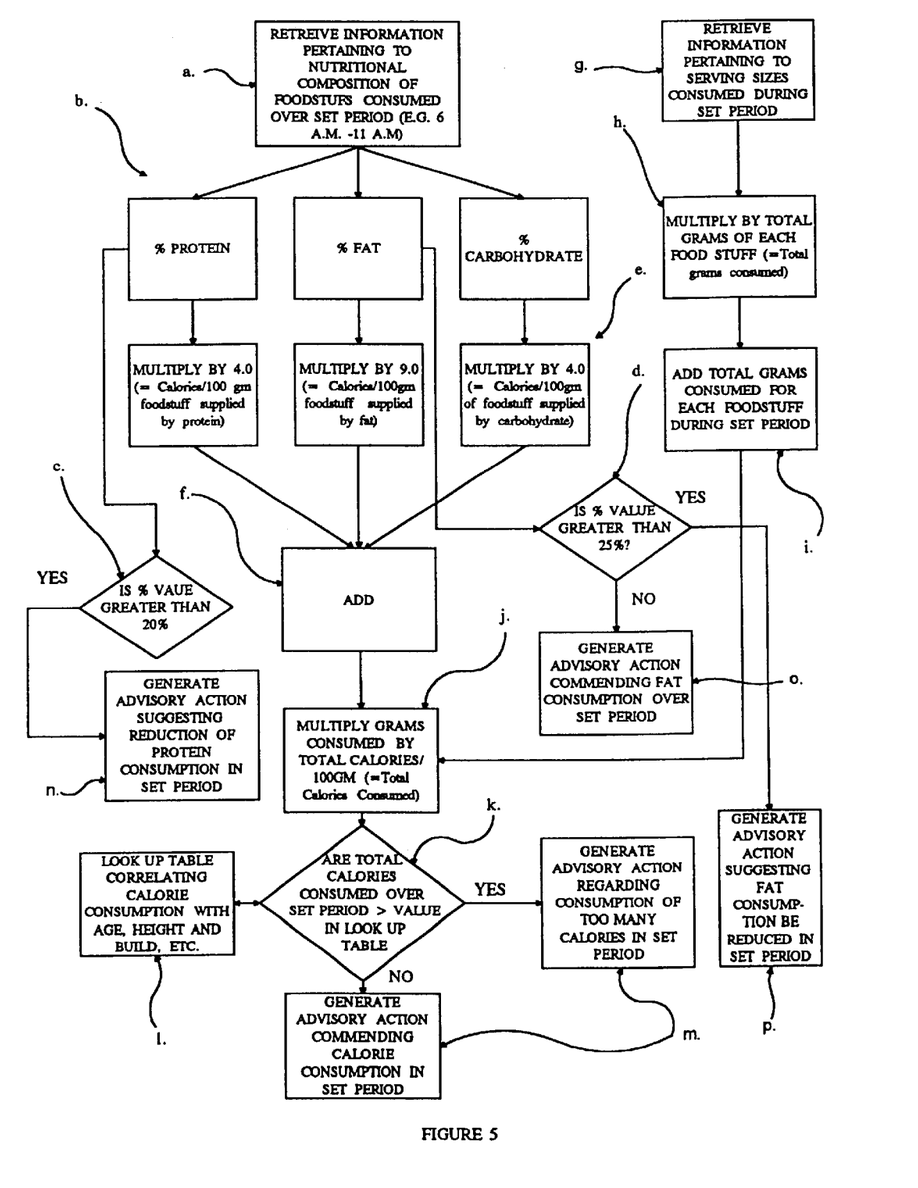
FIG. 5 is a data flow chart of a method by which nutritional advisories pertaining to consumed foodstuffs may be generated.

FIG. 5 illustrates an exemplary data flow chart of a process by which nutritional advisories pertaining to consumed foodstuffs may be generated. Information pertaining to the nutritional composition of the foodstuff identifiers entered over a set period of time is first retrieved (FIG. 5a) as well as information pertaining to the amount of each foodstuff consumed (FIG. 5g,h). The percentage of protein, fat, carbohydrate encompassed by each food stuff, and the totality of foodstuffs eaten during the time period of concern, is determined (FIG. 5b). If the total percentage of the diet during the select period is comprised of more than 20% protein (FIG. 5c) or greater than 25% fat (FIG. 5d), advisories actions suggesting a reduction in protein consumption (FIG. 5n) or in fat consumption (FIG. 5p) are generated. Commendatory advisory actions may also be issued if consumption is within dietary guidelines (FIG. 5o). After determining the total mass of foodstuffs consumed over the period in question (FIG. 5i), total calories consumed may be determined by multiplying the total percentage of protein, fat and carbohydrate by the appropriate conversion multiplicand (FIG. 5e), adding the result (FIG. 5f) and multiplying the same by the total mass of foodstuffs consumed over that period (FIG. 5j). After consultation with a look-up table correlating calorie consumption with parameters such as age, height and build (FIG. 5l), it is determined whether the total calories consumed over the set period is greater than the recommended calorie consumption in the look-up table (FIG. 5k). If the number of calories consumed is greater than the recommended consumption for that time period, an advisory action suggesting reduction in the consumption of foodstuffs over that time period may be generated, or if in the alternative, the consumption is less than that in the look up table (but not extraordinarily so), an advisory action commending calorie intake over than period of time may be generated (FIG. 5m).

Figure 6:
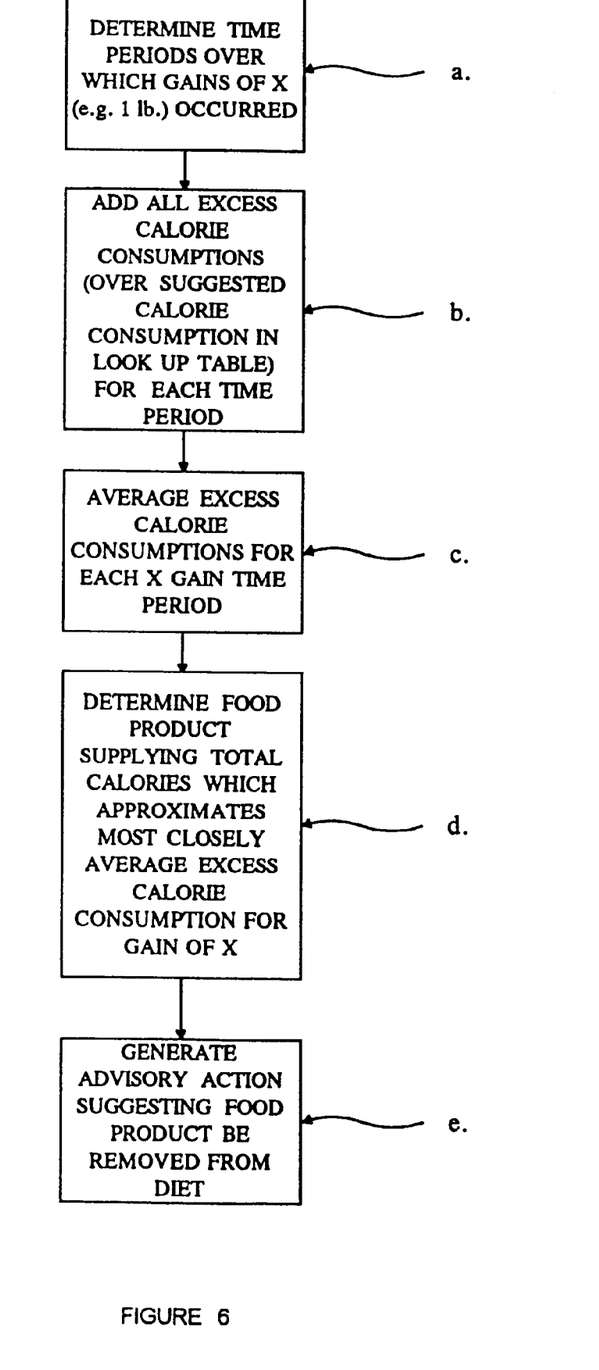
FIG. 6 is a flow chart of a process by which weight control can be effectuated utilizing the invention by removing particular foodstuffs from the diet.

Referring now to FIG. 6, there is shown a flow chart of a process by which weight control can be effectuated utilizing the invention by removing particular foodstuffs from the diet. The period of time over which a particular weight gain occurs is determined (FIG. 6a), as for example 1 pound per 1 month. All excess calorie consumptions within each weight gain period are determined (FIG. 6b), as for example the excess calorie consumptions per month. Average excess calorie consumptions for each weight gain time period is then calculated (FIG. 6c). It is then determined the consumption of which food product most closely approximates the average excess calorie consumption during the weight gain period (FIG. 6d). An advisory action suggesting removal of the food product from the diet is then issued (FIG. 6e).

What is claimed is:

1. A computer-assisted method for retrieving information pertaining to a consumable comprising:

storing in a computer readable data structure consumption information with regard to a consumable having a unique encoded product identifier thereon;

retrieving said consumption information from said computer readable data structure upon receipt of a digital data signal for such consumption information, said digital data signal being initiated by input of said unique encoded product identifier into a computer remote from said computer readable data structure;

transmitting said consumption information to said remote computer.

2. The method as recited in claim 1 further comprising the step of: recording the time of receipt of said digital data signal seeking such consumption information.

3. The method as recited in claim 1 wherein said consumption information relates to the contents of said consumable.

4. The method as recited in claim 1 wherein the consumption information is nutritional information.

5. The method as recited in claim 1 wherein the consumable is a foodstuff.

6. The method as recited in claim 1 wherein the consumable is a drug.

7. The method as recited in claim 1 wherein the consumable is a pre-packaged good.

* * * * *